(12) United States Patent
Eidenschink

(10) Patent No.: US 7,291,127 B2
(45) Date of Patent: Nov. 6, 2007

(54) VARIABLE MANIPULATIVE STRENGTH CATHETER

(75) Inventor: Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 450 days.

(21) Appl. No.: 10/628,998

(22) Filed: Jul. 28, 2003

(65) Prior Publication Data
US 2005/0027244 A1  Feb. 3, 2005

(51) Int. Cl.
*A61M 31/00* (2006.01)
(52) U.S. Cl. .................................... 604/95.05
(58) Field of Classification Search ............... 604/509, 604/510, 96.01, 113, 523–528, 530–532, 604/95.05, 95.01; 606/191, 192, 194; 600/151–152
See application file for complete search history.

(56) References Cited

U.S. PATENT DOCUMENTS

| | | | |
|---|---|---|---|
| 4,758,222 A | 7/1988 | McCoy | 604/95 |
| 4,799,474 A * | 1/1989 | Ueda | 600/151 |
| 4,822,345 A * | 4/1989 | Danforth | 604/524 |
| 5,047,045 A | 9/1991 | Arney et al. | 606/194 |
| 5,156,594 A | 10/1992 | Keith | 604/96 |
| 5,499,973 A | 3/1996 | Saab | 604/96 |
| 5,531,685 A | 7/1996 | Hemmer et al. | 604/95 |
| 5,549,552 A | 8/1996 | Peters et al. | 604/96 |
| 5,662,621 A | 9/1997 | Lafontaine | 604/281 |
| 5,876,373 A * | 3/1999 | Giba et al. | 604/95.04 |
| 5,997,526 A | 12/1999 | Giba et al. | 604/531 |
| 6,030,405 A | 2/2000 | Zarbatany et al. | 606/191 |
| 6,190,355 B1 | 2/2001 | Hastings | 604/96.01 |
| 6,203,558 B1 | 3/2001 | Dusbabek et al. | 606/198 |
| 6,464,683 B1 * | 10/2002 | Samuelson et al. | 604/524 |
| 6,514,237 B1 | 2/2003 | Maseda | 604/533 |
| 6,562,021 B1 | 5/2003 | Derbin et al. | 604/523 |
| 6,575,934 B2 | 6/2003 | Duchamp | 604/102.02 |
| 2001/0039412 A1 | 11/2001 | Fariabi | |
| 2002/0022831 A1 | 2/2002 | O'Connor | |
| 2002/0082549 A1 | 6/2002 | Duchamp | |

FOREIGN PATENT DOCUMENTS

| | | |
|---|---|---|
| EP | 0420 993 | 10/1990 |
| WO | 99/60917 | 12/1999 |
| WO | 02/26175 | 4/2002 |

* cited by examiner

*Primary Examiner*—Catherine S. Williams
(74) *Attorney, Agent, or Firm*—Vidas, Arrett & Steinkraus

(57) ABSTRACT

A catheter assembly comprises a catheter which comprises an inner shaft and an outer shaft, and at least one heat transmitting mechanism. At least one portion of at least one of the inner shaft and the outer shaft of the catheter has a predetermined longitudinal stiffness and a predetermined temperature. The predetermined longitudinal stiffness is changed when the predetermined temperature is changed. The at least one heat transmitting mechanism extends distally from the proximal end of the catheter, along the length of the catheter, to a position adjacent to the at least one portion. At least a portion of the at least one heat transmitting mechanism is constructed and arranged to conductively change the predetermined temperature of the at least one portion of the at least one of the inner shaft and the outer shaft.

37 Claims, 10 Drawing Sheets

VARIABLE MANIPULATIVE STRENGTH CATHETER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

Embodiments of this invention are directed to the field of intravascular medical devices, and more particularly to the field of catheters such as angioplasty, neurological and guide catheters, among others, which may be used in various medical procedures such as percutaneous transluminal angioplasty (PTA), percutaneous transluminal coronary angioplasty (PTCA) as well as in procedures involving the placement of medicines and medical devices within the body.

Some embodiments of the invention are directed to all forms of catheters which may be advanced through a body lumen or vessel. Some examples of catheters are over-the-wire (OTW) catheters, such as are described in U.S. Pat. No. 5,047,045; single-operator-exchange (SOE) balloon catheters, such as are described in U.S. Pat. No. 5,156,594 and U.S. Pat. No. 5,549,552. Other examples of catheters which may incorporate the unique features of the present invention may include rapid-exchange catheters, guide catheters, etc.

2. Description of the Related Art

Intravascular diseases are commonly treated by relatively non-invasive techniques such as PTA and PTCA. These angioplasty techniques typically involve the use of a balloon catheter. In these procedures, a balloon catheter is advanced through the vasculature of a patient such that the balloon is positioned proximate a restriction in a diseased vessel. The balloon is then inflated and the restriction in the vessel is opened. In other uses a catheter may be used to delivery an endoprosthesis such as a stent, graft, stent-graft, vena cava filter or other implantable device or devices herein after collectively referred to as a stent or stents. Where a stent is to be delivered into a body lumen the catheter may include one or more inflatable portions or balloons. Typically, the stent is retained in the pre-delivery state about the catheter shaft, or a portion thereof such as a balloon, by crimping and/or through the use of a retaining mechanism such as sleeve, sheath or sock.

Balloons and balloon catheters may be particularly useful for the delivery of expandable, implantable medical devices such as stents, grafts, stent-grafts, vena cava filters, hereinafter referred to cumulatively as stents. Stents and catheters used in their delivery are commonly used and as such their structure and function are well known.

A stent is a generally cylindrical prosthesis introduced via a catheter into a lumen of a body vessel in a configuration having a generally reduced diameter and then expanded. In its expanded configuration, the stent supports and reinforces the vessel walls while maintaining the vessel in an open, unobstructed condition.

In order to properly position a stent and/or balloon within a body lumen, the catheter must be advanced through the narrow confines of the body. Typically the balloon and/or stent is located near the distal end of the catheter. In order to advance the distal end of most prior catheters further in to a body lumen, the inner shaft or catheter member is utilized to transmit force to the distal end. However, the inner is typically soft and flexible which often results in poor transmission of push.

The present invention, in accordance with the various embodiments presented herein, addresses the shortcoming of poor push transmission common to many catheters.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

The present invention may be embodied in a variety of forms. For example, in at least one embodiment the invention is directed to a catheter assembly having variable stiffness characteristics along its length.

A catheter may be provided with variable stiffness by constructing the inner shaft of the catheter, and/or other portion of the catheter from a temperature sensitive material which may then be affected by selective heating or cooling at least a portion of the material as the catheter is advanced through a vessel or other body lumen.

For example, to provide a portion of the catheter with a variable stiffness a portion of the inner shaft of the catheter is at least partially constructed from a material which has one or more physical properties, such as stiffness, which are changed as a result of exposure to a range of temperatures. For example, when at least a portion of the catheter shaft is cooled by exposure to a coolant the affected portion will become stiffer.

The extent of the stiffening of the material is based on the particular characteristics of the material from which the catheter shaft is constructed as well as the temperature of the fluid to which the material is exposed. The same material may also become less stiff upon exposure of at least a portion of the material to a heated fluid or other temperature elevating mechanism.

In some embodiments the catheter or at least a portion thereof may be constructed of a variety of materials having different temperature sensitivities. As a result one or more portions of the catheter may be provided with varying degrees of stiffness, despite being affected by a similar change in temperature.

In order to provide one or more regions of the catheter shaft, or other catheter component(s), with a coolant, heated fluid, or other temperature affecting mechanism, in some embodiments a catheter may be equipped with one or more lumens through which a fluid is passed. While typically the fluid may have an elevated or reduced temperature relative to the surrounding catheter structure, in some embodiments the presence of the fluid itself within the one or more lumens may act to increase the stiffness of the catheter shaft. By varying the pressure of the fluid within the one or more lumens, and/or the temperature, the stiffness of the catheter may be increased or decreased as desired.

In some embodiments the lumens terminate at a reservoir for containing a predetermined quantity of fluid. One or more reservoirs may be positioned at desired locations along the length of the catheter such as for example at one or more areas adjacent to a balloon mounted on the catheter shaft.

In some embodiments the consistency of the fluid may affect the stiffness of the catheter as well. For example, if a gas or liquid is present in the one or more lumens, the stiffness of the catheter may be increased by cooling the gas or liquid so that it transitions to a gel or even a solid. Where the fluid is a liquid, cooling the liquid to a gel or a solid state will increase stiffness while warming a gelled liquid to a less viscous state will typically reduce stiffness, etc.

In some embodiments the one or more fluid transmission lumens are longitudinally oriented. In at least one embodiment, a portion of one or more lumens may be coiled or otherwise concentrated at one or more regions of the catheter shaft to provide regions which may be selectively stiffer merely by injecting fluid therethrough. The fluid may have an elevated or reduced temperature as desired.

In some embodiments, electrical current may be transmitted along a conductive wire or other member to a portion of the wire that is at least partially electrically resistant in order to produce heat. The heat produced thereby is then conductively or otherwise transmitted to the adjacent portion of the catheter thereby reducing the stiffness of the material in that region. In some embodiments the portion of the wire (or wires) that is at least partially electrically resistant is one or more coils disposed about at least one region of the catheter shaft. In at least one embodiment a portion of the catheter shaft may be constructed from a graphite polymer hybrid material or other electrically conductive polymer(s), such as for example tecophilic material, which may transfer electric current and heat to one or more areas of the catheter. When electric current is directed to the hybrid material by a conductive wire or other device the hybrid material will create heat thereby reducing the stiffness of the catheter in areas adjacent thereto.

In some embodiments the portion of the catheter to be selectively increased in stiffness or decreased in stiffness may be one or more portions of the catheter shaft or any other region of the catheter including at least a portion of a dilatation balloon disposed thereon.

In at least one embodiment a catheter is equipped with one or more lumens for passage of a coolant therethrough, as well as a mechanism for providing heat to at least a portion of the catheter.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
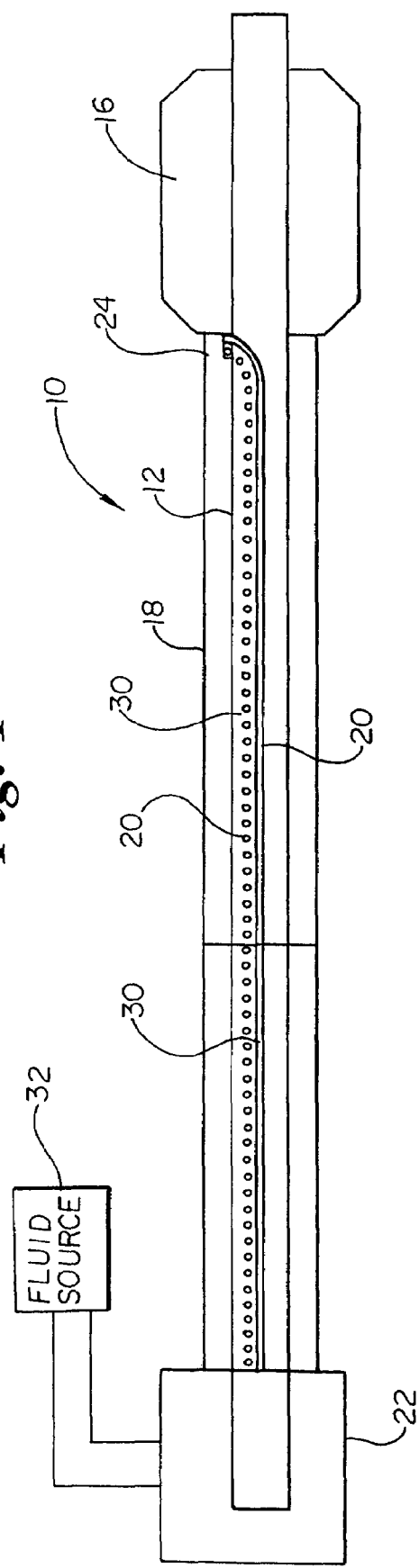
FIG. 1 is a longitudinal cross-sectional view of an embodiment of the invention.

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As indicated above, the present invention may be embodied in a variety of forms. For example, in the embodiment shown in FIG. 1 the invention is directed to a catheter assembly, indicated generally at 10, wherein the catheter 10 is provided with an inner shaft 12 that has a stiffness which may be modified at one or more locations by cooling or heating the desired locations even while the distal end 14 of the catheter 10 is within a patient's body (not shown).

In the embodiment depicted in FIGS. 1-4 the catheter 10 the inner shaft 12 of the catheter, and/or other portion of the catheter such for example one or more portions of the balloon 16 or distal outer shaft 18, may be at least partially constructed from polyethylene (LDPE), high density polyethylene (HDPE), ionomer and a polyether block amide available under the trade name PEBAX™, one or more liquid crystal polymers, one or more ionomers such as a copolymer polyolefin material available from E.I. DuPont de Nemours and Co. (Wilmington, Del.), under the trade name Surlyn™, polytetrafluoro-ethylene (PTFE), or any other suitable material which has a predetermined stiffness that may be varied at different temperatures.

For purposes of the present Application a suitable temperature sensitive material is one which may be provided with an increased stiffness when the material is cooled or a reduced stiffness (softening) when the material is heated.

In some embodiments the catheter or at least a portion thereof may be constructed of a variety of materials having different temperature sensitivities. For example in the cross-sectional views shown in FIGS. 3-4, 7-8 and 10 the inner shaft 12 is provided with a tri-layer construction of three distinct layers.

A first or inner layer 21 of the shaft 12 defines a guide wire lumen 19. In the embodiment shown the inner layer 21 is at least partially constructed of a material that will provide improved wire movement. Typically, the inner layer is HDPE or a similar material. Where the inner layer 21 is HDPE, a second or middle layer 23 is a thin layer anhydride modified linear low density polyethylene available under the trade name PLEXAR or a similar material suitable for preventing delamination of the inner layer 21 from the outer layer 25. Outer layer 25 is a material which will undergo an order/disorder transformation during a change in the materials temperature. Such outer layer 25 materials may be Pebax, LCPs, Surlyn and/or other materials as well.

If desired, the catheter may be provided with a construction such that different portions of the inner shaft 12 are constructed of different temperature sensitive materials. In such an embodiment different sections of the shaft 12 may have different stiffness properties despite being cooled or heated to the same extent as surrounding portions of the shaft 12.

Figure 2:
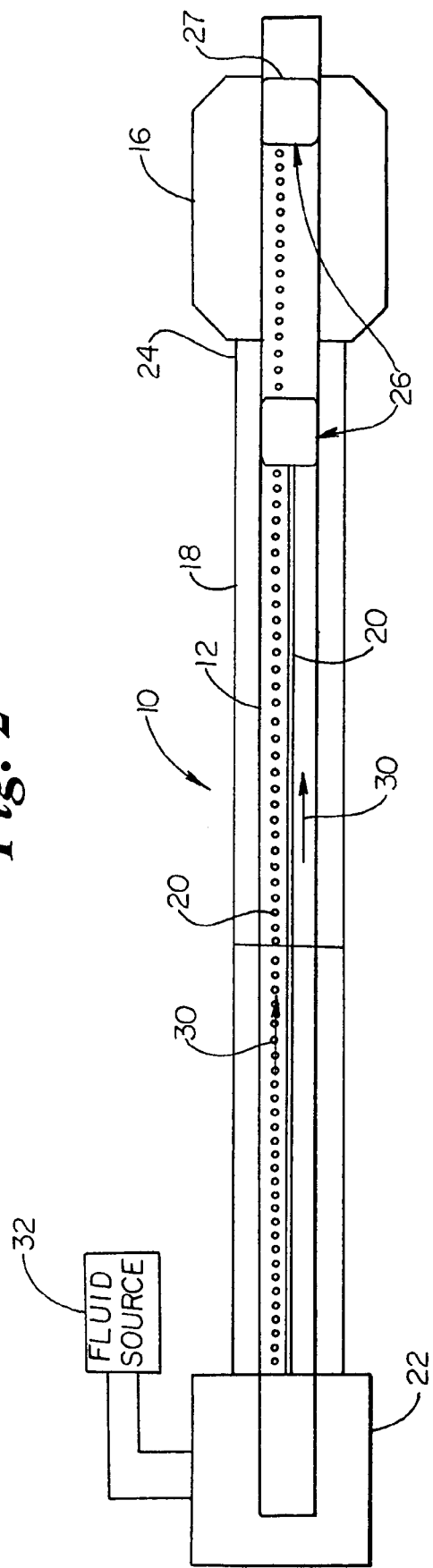
FIG. 2 is a longitudinal cross-sectional view of the embodiment shown in FIG. 1 wherein each lumen includes a fluid reservoir.

In order to provide one or more regions of the catheter 12, or other catheter component(s) such as the balloon 16 and distal outer shaft 18, with a coolant, heated fluid, or other temperature affecting fluid, the catheter 10 defines one or more fluid transport lumens 20 which extend through the length of the catheter 10 from the proximal end or manifold 22 of the catheter to predetermined location within the distal portion 24 of the catheter 10, such as is shown in FIGS. 1-2.

Lumens 20 are constructed and arranged to transport a fluid, indicated by arrows 30, that has been heated or cooled to a predetermined temperature selected for the purpose of affecting the stiffness of the material of the catheter component(s), such as for example the inner shaft 12, adjacent to the lumen 20. In some embodiments where fluid 30 is heated, the fluid 30 may have a temperature of about 10 degrees Celsius above body temperature (about 37 degrees C.), in some embodiments the heated fluid 30 is about 13 degrees C. to about 23 degrees C. above body temperature, or about 50 degrees C. to about 60 degrees C. In embodiments where the fluid 30 is cooled or has an inherently cool temperature, relative to body temperature, the fluid may have a temperature of about 15 degrees C. to about −195 degrees C. In at least one embodiment the fluid 30 is at least partially comprised of a solution of liquid Nitrous Oxide ($N_2O$).

It is noted however, that fluid 30 may be comprised of any fluid desired, and that fluid 30 may be provided with a temperature other than those provided above. Depending on the particular temperature and material characteristics of the fluid 30, the catheter 10 and components thereof may be provided with insulative and/or other characteristics to minimize any affect that such fluid or temperature could potentially have on the surrounding anatomy through which the catheter is passed.

The fluid 30 is transported from a fluid source 32, located at or adjacent to the manifold 22 and which is in fluid communication with the lumens 20, along the length of the catheter 10 through the lumens 20. The fluid 30 will conductively transmit heat to or from the adjacent catheter components, such as for example the inner shaft 12, thereby heating or cooling the shaft 12 to affect the stiffness of the shaft 12 to a desired extent.

The lumens 20 are typically constructed from a polyamide tube, a surlyn sheath or wall 29 and/or other similar material having a wall thickness of about 0.002 inches or less and in some embodiments 0.001 inches or less. The lumens 20 define an inner diameter of about 0.002 inches to about 0.008 inches. In some embodiments the inner diameter of the lumens 20 is about 0.003 inches.

Figure 3:
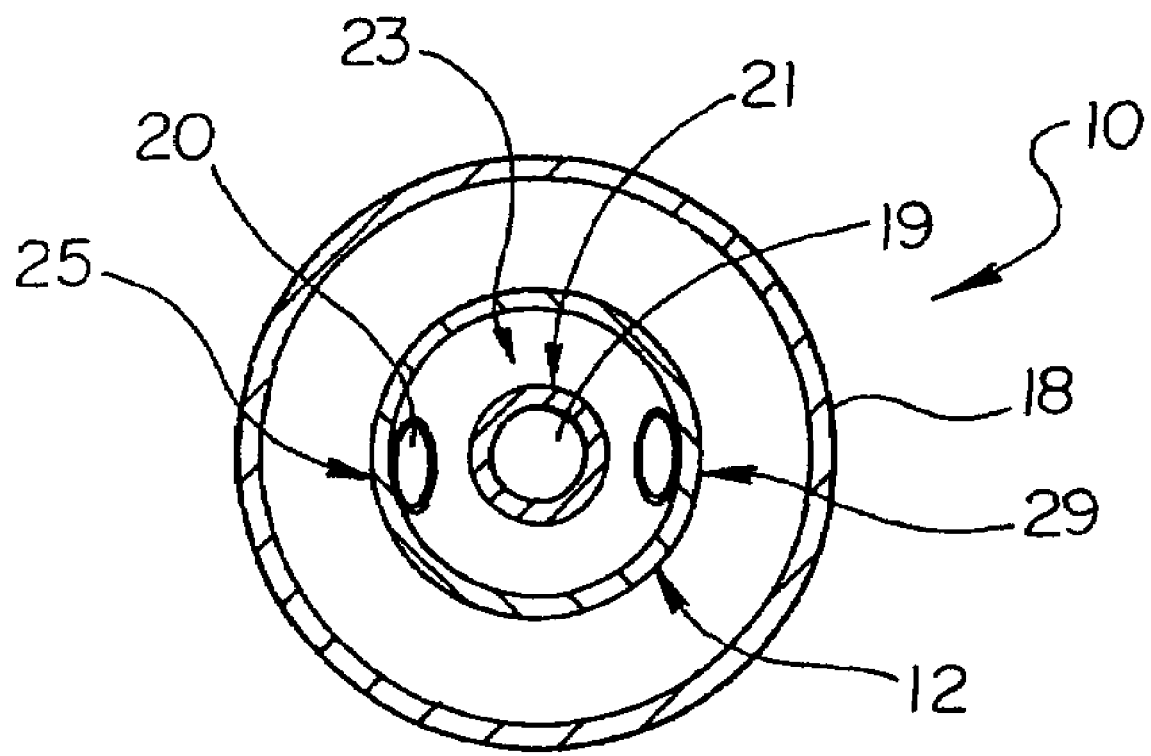
FIG. 3 is a cross-sectional view of the embodiment shown in FIG. 1 wherein the transport lumen is shown within the wall of the inner shaft.
Figure 4:
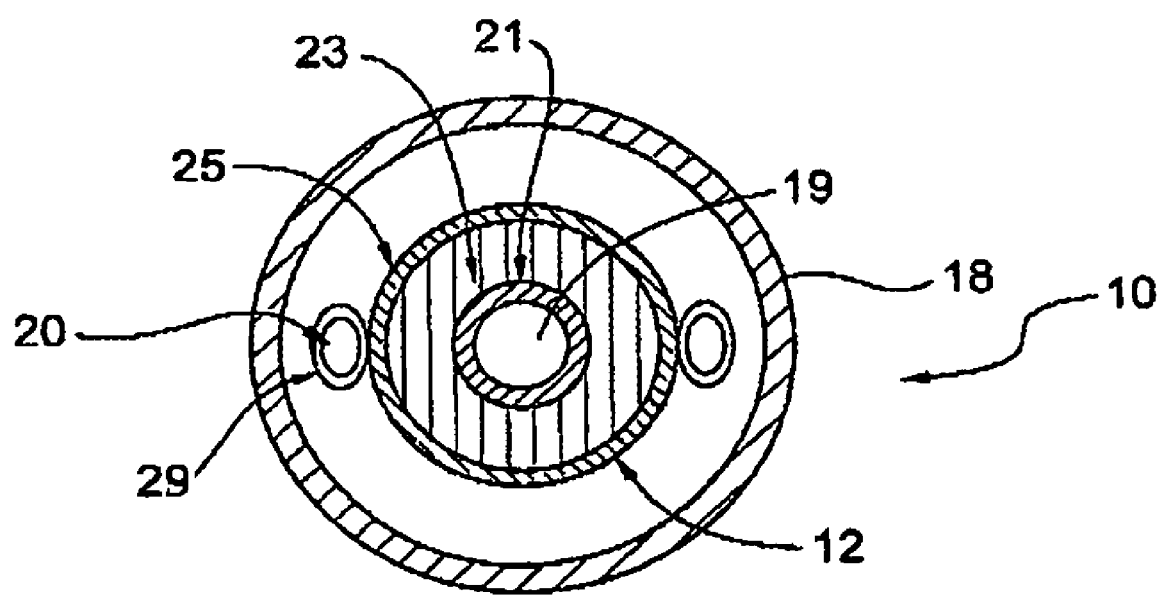
FIG. 4 is a cross-sectional view of the embodiment shown in FIG. 1 wherein the transport lumen is shown external of the inner shaft.

As is shown in FIG. 3, lumens 20 may be contained within or at least partially defined by the inner shaft 12. In some embodiments however, at least a portion of the lumen 20 is a distinct tubular structure external of the inner shaft 12 as is shown in FIG. 4.

In some embodiments the one or more fluid transmission lumens 20 are longitudinally oriented. In at least one embodiment however, at least a portion of one or more of the lumens may be coiled or otherwise distributed in a manner so as to concentrate the heating and/or affect of the fluid on an adjacent region of the catheter.

Typically the fluid 30 will be provided with an elevated or reduced temperature relative to the surrounding catheter structure of for example the inner shaft 12. It should be recognized however, that in some embodiments the presence of the fluid 30 itself, within the one or more lumens 20, may act to increase the stiffness of the inner shaft 12 merely by increasing the turgidity of the lumens 20 along the longitudinal length of the catheter 10. By varying the pressure of the fluid within the one or more lumens 20 the turgidity of the lumen and thus the stiffness of the catheter may be increased or decreased as desired.

In some embodiments the consistency or viscosity of the fluid 30 may affect the stiffness of the catheter 10 as well. For example, if a liquid or even a gas is present in the one or more lumens 20 under low pressure, the stiffness of the catheter 10 may be increased by cooling the fluid 30 so that it transitions to a more viscous liquid or gel-like state, or even to a solid form. Where the fluid 30 is a liquid, cooling the liquid to a gel or a solid state will increase stiffness while warming a gelled liquid to a less viscous state will typically reduce stiffness, etc.

In some embodiments, such as is shown in FIG. 2 the lumens 20 terminate at one or more reservoirs 26 which are enlarged areas, relative to the diameter of each lumen 20, where the heated or cooled fluid 30 may collect to concentrate the heating and/or cooling affect of the fluid 30 at one or more predetermined locations. One or more reservoirs 26 may be positioned at desired locations along the length of the catheter 10 such as for example at one or more areas adjacent to a balloon 16 about the inner shaft 12.

In some embodiments where the catheter 10 is to be utilized for the delivery of an endoprosthesis such as a stent, at least a portion of the balloon 16 may define a stent mounting region.

Reservoirs 26 may be merely an enlarged extension of each lumen 20. In some embodiments however, reservoirs 26 comprise a fluid permeable membrane 27 which holds fluid 30. In some embodiments, the membrane 27 may comprise a fluid absorbing gel or other medium.

In some embodiments of the invention, examples of which are illustrated in FIGS. 5-10, the catheter 10 may be equipped with one or more electrically conductive members or wires 34 which are configured to transmit electric current, indicated by arrows 35, to one or more resistive coils or heating elements 36. Heating elements 36 may be distributed about or adjacent to any portion of the catheter 10 or its components, including the inner shaft 12, balloon 16, and/or distal outer shaft 18.

Figure 5:
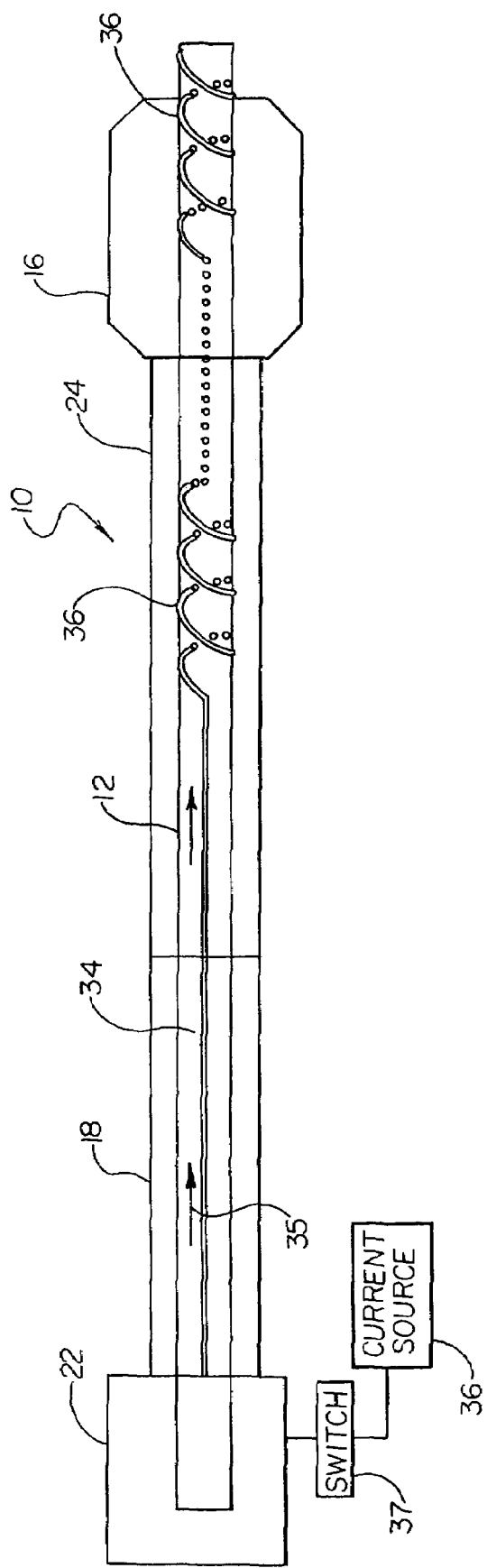
FIG. 5 is a longitudinal cross-sectional view of an embodiment of the invention.
Figure 6:
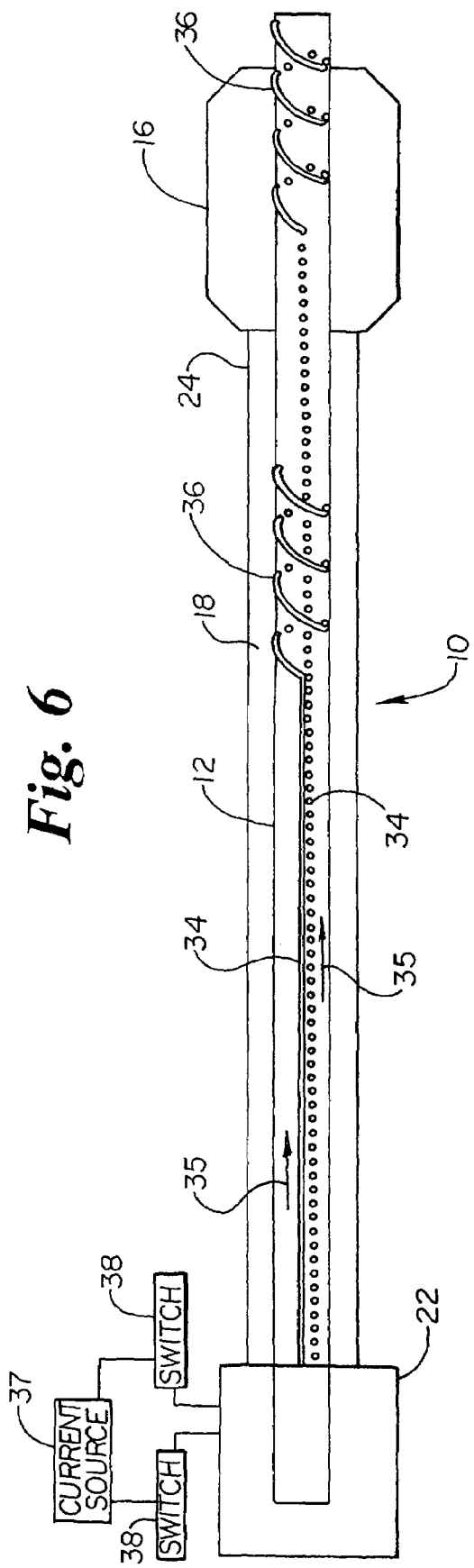
FIG. 6 is a longitudinal cross-sectional view of the embodiment shown in FIG. 5 wherein two separate conductive members are utilized.
Figure 7:
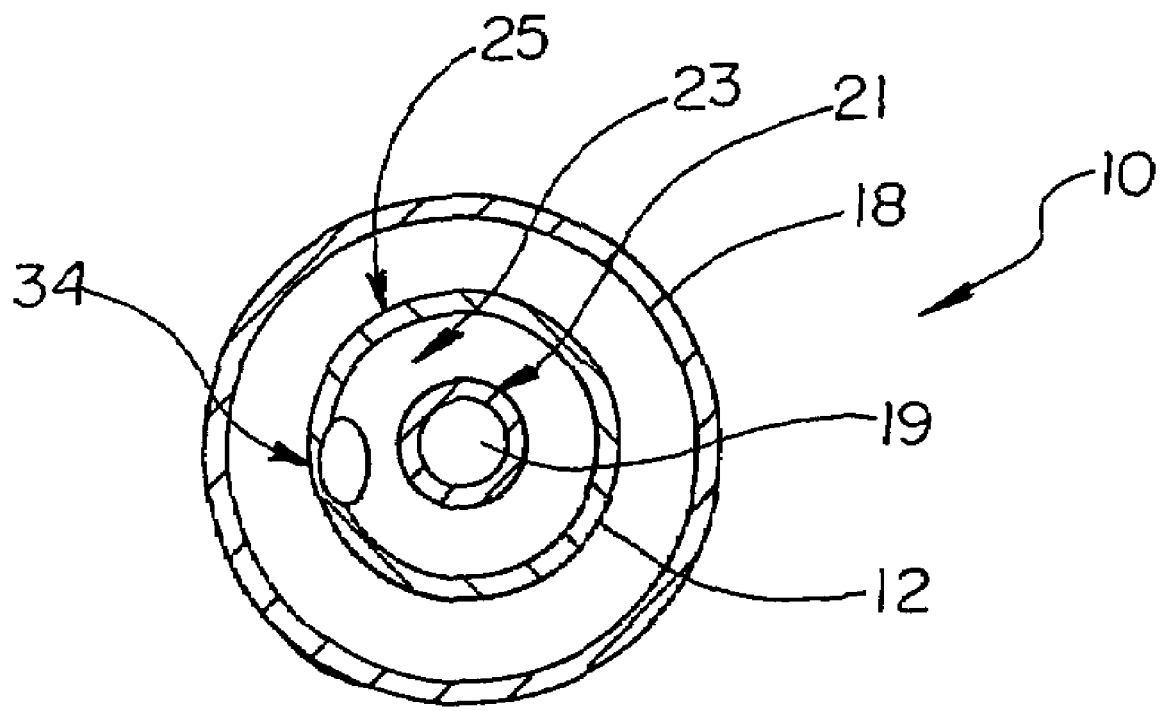
FIG. 7 is a cross-sectional view of the embodiment shown in FIG. 5 wherein the conductive wire is shown within the wall of the inner shaft.
Figure 8:
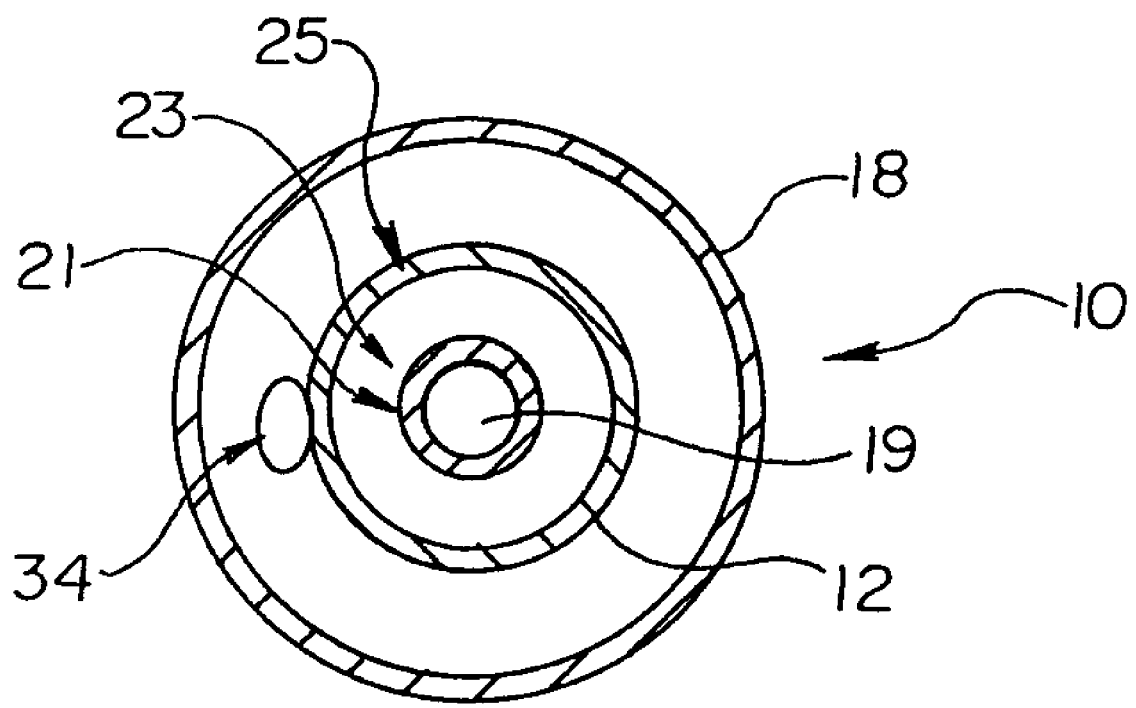
FIG. 8 is a cross-sectional view of the embodiment shown in FIG. 5 wherein the conductive wire is shown external of the inner shaft.

For example, in the embodiment shown in FIG. 5 a single conductive wire 24 extends distally from a power source 36 and switch 37 located at or adjacent to the manifold 22 of the catheter 10. The wire 34 is conductively engaged to at least one heating element 36 and in some embodiments multiple heating elements 36. The wire 34 may be at least partially contained within the inner shaft 12 such as is shown in FIG. 7, or may be positioned adjacent thereto such as is shown in FIG. 8. A draw back to providing a catheter 10 with multiple heating elements 36 and only a single wire 34 is that in such an embodiment it may be difficult to effect heating of only one of the regions adjacent to a coil and not the other. To provide a catheter where selected region may be heated exclusively or in conjunction with other regions, each element 36 may be independently electrified by its one dedicated wire 34 such as is shown in FIG. 6. Electric current may be provided to one or more wires by separate switches 37.

In some embodiments catheter components such as shafts 12 and 18 as well as balloon 16 may be at least partially constructed of a polymer graphite hybrid material. Such a material at least partially conducts an electric current transmitted thereto thereby allowing the material of the selected catheter component to act as a heating element 36.

In some embodiments, the heating element 36 is a coiled member disposed in a spiral, helical or other configuration about the inner shaft 12 of the catheter 10. However, the heating element 36 as well as the wire 34 may be longitudinally parallel to the longitudinal axis of the catheter, or have any other configuration desired. For example, where a greater concentration of heat is desired, the coils of a particular heating element may be more numerous and/or more tightly wound about the inner shaft 12 whereas another coil may only comprise a few widely spaced coils as desired.

Figure 9:
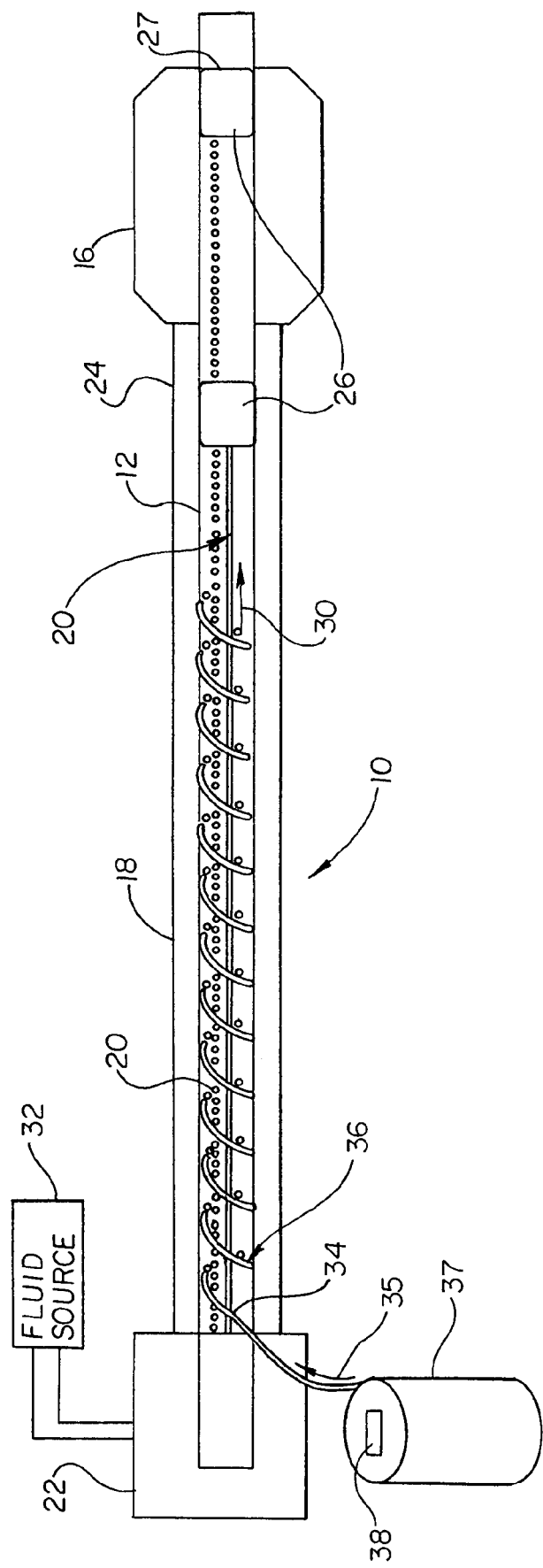
FIG. 9 is a longitudinal cross-sectional view of an embodiment of the invention.
Figure 10:
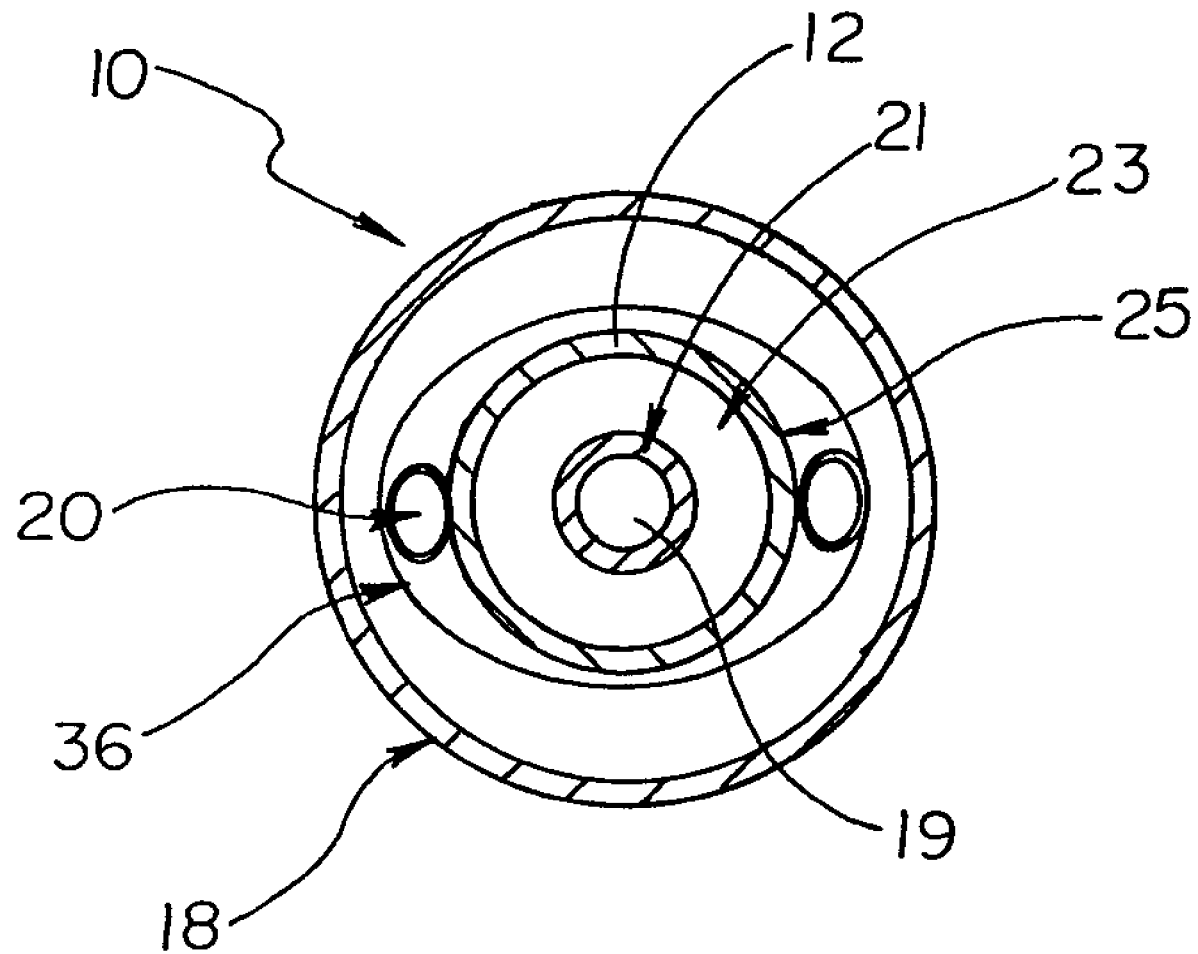
FIG. 10 is a cross-sectional view of the embodiment shown in FIG. 9 wherein a coiled heating element is utilized in conjunction with at least one fluid transport lumen.

In at least one embodiment, such as is illustrated in FIGS. 9 and 10, the catheter 10 may comprise a combination of one or more lumens 20, with or without reservoirs 26, as well as one or more wires 34 and their associated heating elements 36. While the elements 36 and/or lumens 20 may be at least partially imbedded within or external to the inner catheter 12, in the embodiment shown in FIG. 10 however the element 36 is disposed about the inner shaft 12 and the lumens 20 are positioned between the element 36 and the shaft 12. Alternative configurations may be utilized as desired.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A catheter assembly comprising:
   a catheter, the catheter having a length that extends distally from a proximal end, the catheter comprising an inner shaft constructed of at least three layers, a lumen wall, an outer shaft, and at least one heat transmitting mechanism, the at least one heat transmitting mechanism comprising at least one fluid transmission lumen defined only by the lumen wall, the lumen wall positioned between the inner shaft and the outer shaft,
   at least one portion of at least one of the inner shaft and the outer shaft of the catheter having a predetermined longitudinal stiffness, the at least one portion having a predetermined temperature, the predetermined longitudinal stiffness being changed when the predetermined temperature is changed.

2. The assembly of claim 1 wherein the at least one heat transmitting mechanism extends distally from the proximal end along the length of the catheter to a position adjacent to the at least one portion, at least a portion of the at least one heat transmitting mechanism constructed and arranged to conductively change the predetermined temperature of the at least one portion.

3. The assembly of claim 1 the at least one fluid transmission lumen constructed and arranged to transport a fluid having a temperature different than the predetermined temperature of the at least one portion from the proximal end of the catheter to the position adjacent to the at least one portion.

4. The assembly of claim 3 wherein the fluid has a temperature greater than that of the predetermined temperature of the at least one portion.

5. The assembly of claim 4 wherein the at least one heat transmitting mechanism is constructed and arranged to conductively transmit heat from the fluid to the at least one portion.

6. The assembly of claim 3 wherein the fluid has a temperature less than that of the predetermined temperature of the at least one portion.

7. The assembly of claim 6 wherein the at least one heat transmitting mechanism is constructed and arranged to conductively transmit heat from the at least one portion to the fluid.

8. The assembly of claim 1 further comprising a fluid source in fluid communication with the at least one fluid transmission lumen.

9. The assembly of claim 1 wherein the lumen wall is at least partially constructed from at least one material selected from the group consisting of polyamide, copolymer polyolefin, polyethylene, and any combination thereof.

10. The assembly of claim 1 the lumen wall having a thickness of about 0.002 inches or less.

11. The assembly of claim 1 the lumen wall having a thickness of about 0.001 inches or less.

12. The assembly of claim 1 wherein the at least one fluid transmission lumen has an inner diameter of about 0.002 inches to about 0.008 inches.

13. The assembly of claim 1 wherein the at least one fluid transmission lumen has an inner diameter of about 0.003 inches.

14. The assembly of claim 9 wherein the lumen wall is at least partially contained within the inner shaft.

15. The assembly of claim 9 wherein the lumen wall is immediately adjacent to the inner shaft.

16. The assembly of claim 9 wherein the lumen wall is immediately adjacent to the outer shaft.

17. The assembly of claim 3 wherein the fluid is a liquid.

18. The assembly of claim 1 wherein the at least one portion of at least one of the inner shaft and the outer shaft of the catheter is at least partially constructed from a member of the group consisting of polyethylene (LDPE), high density polyethylene (DEPE), ionomer and a polymer ether block amide, one or more liquid crystal polymers, one or more ionomers, polytetrafluoro-ethylene (PTFE) and any combination thereof.

19. The assembly of claim 1 wherein the at least three layers comprise:
a first layer, the first layer defining a guide wire lumen, the first layer being at least partially constructed from HDPE.

20. The assembly of claim 19 wherein the at least three layers comprise:
a second layer of anhydride modified linear low density polyethylene, the first layer being engaged to the second layer.

21. The assembly of claim 20 wherein the at least three layers comprise:
a third layer, the third layer at least partially constructed of at least one third layer material exhibiting an order/disorder transformation during a change in the temperature of the at least one third layer.

22. The assembly of claim 21 wherein the at least one third layer material is selected from at least one member of the group consisting of polyether block amide, LCP, copolymer polyolefin, and any combination thereof.

23. The assembly of claim 1 further comprising a balloon, the balloon being engaged to at least a portion of at least one of the inner shaft and outer shaft.

24. The assembly of claim 23 wherein at least a portion of the balloon defines a stent mounting region.

25. The assembly of claim 1 wherein the at least one heat transmitting mechanism comprises at least one electrically conductive member and at least one at least one heating element positioned adjacent to the at least one portion.

26. The assembly of claim 25 wherein the at least one electrically conductive member extending from the at least one heating element to a source of electrical current positioned adjacent to the proximal end of the catheter, the at least one electrically conductive member in selective electronically conductive communication with the source of electric current and the at least one heating element.

27. The assembly of claim 26 wherein when an electric current is communicated to the at least one heating element, the at least one heating element produces heat.

28. The assembly of claim 27 wherein the at least one heat transmitting mechanism is constructed and arranged to conductively transmit heat from the at least one heating element to the at least one portion.

29. The assembly of claim 28 wherein the at least one heat transmitting mechanism further comprises at least one fluid transmission lumen, the at least one fluid transmission lumen constructed and arranged to transport a fluid having a temperature different than the predetermined temperature of the at least one portion from the proximal end of the catheter to the position adjacent to the at least one portion.

30. The assembly of claim 29 wherein the fluid has a temperature less than that of the predetermined temperature of the at least one portion.

31. The assembly of claim 30 wherein the at least one fluid transmission lumen conductively transmits heat from the at least one portion to the fluid.

32. The assembly of claim 1 wherein the temperature of the fluid is at least about 10 degrees Celsius warmer than human body temperature.

33. The assembly of claim 1 wherein the temperature of the fluid is at least about 10 degrees Celsius cooler than human body temperature.

34. The assembly of claim 1 wherein the temperature of the fluid is at least about 25 degrees Celsius cooler than human body temperature.

35. The assembly of claim 1 wherein the temperature of the fluid is about 50 degrees Celsius to about 60 degrees Celsius.

36. The assembly of claim 1 wherein the temperature of the fluid is about 15 degrees Celsius to about −195 degrees Celsius.

37. The assembly of claim 1 wherein the fluid is at least partially comprised of Nitrous Oxide.

* * * * *